United States Patent
Li

(10) Patent No.: US 6,268,552 B1
(45) Date of Patent: *Jul. 31, 2001

(54) TRANSGENIC SEEDLESS FRUIT COMPRISING AGL OR GH3 PROMOTER OPERABLY LINKED TO ISOPENTENYL TRANSFERASE OR TRYPTOPHAN MONOOXYGENASE CODING DNA

(75) Inventor: Yi Li, Mansfield Center, KS (US)

(73) Assignee: Kansas State University Research Foundation, Manhattan, KS (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/073,587

(22) Filed: May 6, 1998

Related U.S. Application Data

(60) Provisional application No. 60/045,725, filed on May 6, 1997.

(51) Int. Cl.[7] ............................. A01H 5/00; A01H 5/10; C12N 15/82

(52) U.S. Cl. ............................. 800/317.4; 435/320.1; 800/278; 800/284; 800/298; 800/307; 800/308

(58) Field of Search ................ 435/69.1, 320.1, 435/419, 468; 536/23.2, 23.6; 800/278, 287, 298, 307, 308, 317.4, 317.3, 315, 316, 310, 317.2, 323.2, 317, 317.1, 284

(56) References Cited

U.S. PATENT DOCUMENTS

| | | |
|---|---|---|
| 5,175,095 | 12/1992 | Martineau et al. ............ 435/69.1 |
| 5,422,259 * | 6/1995 | De Both et al. ............ 435/172.3 |
| 5,496,732 | 3/1996 | Smigocki et al. ............ 435/320.1 |

FOREIGN PATENT DOCUMENTS

| | | | |
|---|---|---|---|
| WO 96/00291 | 1/1996 | (WO) | C12N/15/82 |
| WO 97/30165 | 8/1997 | (WO) | C12N/5/00 |
| WO 97/40179 | 10/1997 | (WO) | C12N/15/82 |
| WO 97/41240 | 11/1997 | (WO) | C12N/9/02 |

OTHER PUBLICATIONS

Choi PS, et al. "Genetic transformation and plant regeneration of watermelon using Agrobacterium tumefaciens." Plant Cell Rep. 13:344–348, 1994.*

Martineau et al. (1995) "Production of High Solids Tomatoes Through Molecular Modification of Levels of the Plant Growth Regulator Cytokinin" Bio/Technology 13:250–253.

Rotino et al. (1997) "Genetic engineering of parthenocarpic plants" Nature Biotechnology 15:1398–1401.

Barg, R. "Two approaches to genetically engineered parthenocarpy", (1996), Plant Physiol., 111(2 suppl.):59, #161.

Chiang, H–H. et al. "Isolation of the ArabidopsisGA4 locus", (1995), Plant Cell, 7:195–201.

Evans, M.L. et al. "Functions of Hormones at the Organ Level of Organization", Hormonal Regulation of Development II, 5.8 Fruit Setting and Development, Pp. 195–201, (1984), Springer–Verlag, Berlin.

Hagen, G. "Auxin–induced expression of the soybean GH3 promoter in transgenic tobacco plants", (1991), Plant Mol. Biol., 17:567–579.

Jacobsen, S.E. et al. "SPINDLY, a tetratricopeptide repeat protein involved in gibberellin signal transduction in Arabidopsis", (1996), Proc. Natl. Acad. Sci., 93:9292–9296.

Li, Y. et al. "Altered morphology in transgenic tobacco plants that overproduce cytokinins in specific tissues and organs", (1992), Dev. Biol., 153:386–395.

Li, Y. et al. "An auxin–inducible element in soybean SAUR promoters", (1994), Plant Physiol., 106:37–43.

Li, Y. et al. "Transgenic tobacco plants that overproduce cytokinins show increased tolerance to exogenous auxin and auxin transport inhibitors", (1994), Plant Science, 100:9–14.

Li, Y. et al. "Auxin physiology and expression of the GH3 promoter–gus fusion gene", (1993), Plant Physiol., 102(1 suppl.):25, # 127.

Li, Y. et al. "Identification of an auxin response element (AUXRE) in soybean SAUR promoters", (1994), Plant Physiol., 105(1 suppl.):73, # 361.

Li, Q. and Li, Y. "Isolation of arabidopsis mutants with elevated expression of the auxin inducible GH3 gene", (1996), Plant Physiol., 111(2 suppl.):114, # 467.

Li, Y. et al. "Altered floral organ identity and flower bud formation in transgenic plants that overproduce cytokinins", (1996), Plant Physiol. 111(2 suppl.):59, # 159.

Pear, J.R. et al. "Isolation and characterization of a fruit–specific cDNA and the corresponding genomic clone from tomato", (1989), Plant Mol. Biol., 13:639–651.

Salts, Y. et al. "Sequence coding for a novel proline–rich protein preferentially expressed in young tomato fruit", (1991), Plant Mol. Biol., 17:149–150.

(List continued on next page.)

Primary Examiner—Amy J. Nelson
(74) Attorney, Agent, or Firm—Greenlee, Winner and Sullivan P.C.

(57) ABSTRACT

The present invention provides methods and DNA constructs for the genetic engineering of plant cells to produce plants which produce substantially seedless fruit in the absence of exogenous growth factors (auxins or cytokinins) and in the absence of pollination. The substantially seedless fruits produced by the methods described herein are about the size of wildtype seeded fruit (or somewhat larger) and these fruits are equal to or superior to the wildtype seeded fruit with respect to solid content and flavor. The seedless fruits of the present invention are produced in transgenic plants which contain and express auxin or cytokinin biosynthetic genes, e.g., tryptophan oxygenase or isopentenyl transferase coding sequences expressed under the regulatory control of GH3 or AGL promoter sequences directing preferential or tissue specific expression of a downstream gene in the ovaries or developing fruit.

40 Claims, 4 Drawing Sheets-

OTHER PUBLICATIONS

Savidge, B. et al. "Temporal relationship between the transcription of two arabidopsis MADS box genes and the floral organ identity genes", (1995), *Plant Cell*, 7:721–733.

Schmülling, T. et al. "Single genes from *Agrobacterium rhizogenes* influence plant development", (1988), *EMBO J.*, 7(9):2621–2629.

Sedgley, M. et al., "Early fruit development in the watermelon: Anatomical comparison of pollinated, auxin–induced parthenocarpic and unpollinated fruits", (1977), *Ann. Bot.*, 413:1345–1355.

Sedgley, M. "Ovule and seed growth in pollinated and auxin–induced parthenocarpic watermelon fruits", (1979), *Ann. Bot.*, 43:135–140.

Sitbon, F. et al. "Transgenic Plants Overproducing IAA—A Model System to Study Regulation of IAA Metabolism", (1992), Swedish University of Agricultural Sciences, Umea, Sweeden, Pp. 6–59.

Slightom, J.L. et al. "Nucleotide sequence analysis of TL–DNA of *Agrobacterium rhizogenes* agropine type plasmid", (1986), *J. Biol. Chem.*, 261(1):108–121.

Smigocki, A.C. and Honeczy, I.J. "Cytokinin effects on tomato seed quality, fruit yield, and ripening in transgenic plants carrying the ipt gene", (1992), *HortScience*, 27(6):661, # 648 (PS 10).

Sun, T–p. and Kamiya, Y. "The Arabidopsis GA1 Locus Encodes the cyclase ent–Kaurene synthetase A of gibberellin biosynthesis", (1994), *Plant Cell*, 6:1509–1518.

van Altvorst, A.C. et al. "Effects of the introduction of *Agrobacterium rhizogenes rol* genes on tomato plant and flower development", (1992), *Plant Science*, 83:77–85.

Wareing, P.F. and Phillips, I.D.J. "Hormonal Control in the Whole Plant", *Growth and Differentiation in Plants*, 5.7.1 Fruit Set, Pp. 129–130, (1981), Pergamon Press, Oxford.

Xu, Y–L. et al. "The GA5 locus of *Arabidopsis thaliana* encodes a multifunctional gibberellin 20 oxidase: Molecular cloning and functional expression", (1995), *Proc. Natl. Acad. Sci. USA*, 92:6640–6644.

\* cited by examiner

TRANSGENIC SEEDLESS FRUIT COMPRISING AGL OR GH3 PROMOTER OPERABLY LINKED TO ISOPENTENYL TRANSFERASE OR TRYPTOPHAN MONOOXYGENASE CODING DNA

CROSS REFERENCE TO RELATED APPLICATIONS

This application claims priority from U.S. Provisional Application No. 60/045,725, filed May 6, 1997.

ACKNOWLEDGEMENT OF FEDERAL RESEARCH SUPPORT

This invention was made, at least in part, with funding from the United States Department of Agriculture and the National Aeronautics and Space Administration. Accordingly, the United States Government may have certain rights in this invention.

THE BACKGROUND OF THE INVENTION

The invention relates generally to genetic engineering and, more particularly, to a means and method for making plants which produce substantially seedless fruit, wherein the seedless fruit has desirable taste and size characteristics, rendering it more appealing than naturally occurring fruit to the consumer.

Parthenocarpy, the production of seedless fruits, can be achieved by the addition of the plant growth regulators auxin, cytokinin or gibberellin in many crop species (see, e.g., Naylor (1984) in *Hormonal Regulation of Development II: the functions of hormones from the levels of the cell to the whole plant*, Scott, T., ed., pp. 172–218, Springer-Verlag). Applications of these hormones to the unfertilized flowers of tomato, pepper, tobacco, holly, fig, cucumber, watermelon, avocado, eggplant, pear, blackberry and many other species, induced fruit set in the absence of pollen.

It has been shown that the exogenous application of auxin or gibberellin to unfertilized flowers in a number of plant species, including tomato (*Lysopersicon esculentum*) induces fruit set in the absence of pollination, resulting in the production of parthenocarpic fruit [Wareing and Phillips (1981) *Growth and Differentiation in Plants*, Pergamon Press, Oxford, UK]. By contrast, the exogenous application of cytokinin to ovaries or developing fruits is less effective for the production of seedless fruits. It is believed that exogenously applied cytokinin cannot reach the site of action for fruit development because the hormone is immobile within the plant.

In previous efforts to produce seedless fruits, traditional plant breeding and exogenous application of hormones have been used with some success. However, the exogenous application of plant hormones is a labor-intensive process, and traditional plant breeding is a long term process. Moreover, at least some of the previous attempts to produce certain seedless fruits have resulted in low numbers of seedless fruits and/or in relatively small seedless fruits as compared with the normal, seeded fruits.

There is a long felt need in the art for an effective and economical means and methods for the production of seedless fruit, particularly in good yield and quality as compared with prior art seedless fruits.

SUMMARY OF THE INVENTION

It is an object of the present invention to provide compositions and methods for the production of seedless fruit by transgenic means. This is accomplished by the stable introduction into the plant genome of an expression cassette in which a gene encoding an enzyme involved in the biosynthetic pathway of a plant developmental regulator (cytokinin, auxin or gibberellic acid) is operably linked to transcription control sequences which mediate expression of the linked gene in the proper plant part at the appropriate time during development. As specifically exemplified herein, the gene encodes tryptophan oxygenase (iaaM gene) or isopentenyl transferase (ipt gene), and the transcriptional regulatory sequences are those from the GH3 gene, directing tissue-specific expression of a downstream coding sequence in the ovary and developing fruit. The nucleotide sequence of a specifically exemplified GH3 regulatory region from *Glycine max* is given in SEQ ID NO:1. Other regulatory sequences which mediate selective expression in the ovary and/or developing fruit can be substituted for the GH3 regulatory and promoter sequences, such as the AGL5 or PLE 36 transcriptional control sequences.

Also provided by the present invention is an expression cassette can be expressed in plant tissue after the introduction of the cassette into plant tissue. A preferred coding sequence of interest is that for an auxin biosynthetic enzyme, a gibberellin biosynthetic gene or a cytokinin biosynthetic enzyme. The specifically exemplified coding sequence and deduced amino acid sequence for the auxin biosynthetic enzyme (tryptophan oxygenase), are given in SEQ ID NOs:2 and 3, respectively. The specifically exemplified coding sequence and deduced amino acid sequences of the cytokinin biosynthetic enzyme (isopentenyl transferase) are given in SEQ ID NO:4 and 5, respectively. Transcription is regulated by an ovary and developing fruit specific and auxin-inducible transcriptional regulatory sequence (GH3, from *Glycine max*), as specifically exemplified herein. The AGL5 promoter (See SEQ ID NO:7) (from *Arabidopsis thaliana*) operably linked to an iaaM or ipt coding sequence, also functions in the present invention. It is understood that other tissue-specific regulatory sequences which direct expression of an operably linked coding sequence in the developing ovary or developing fruit can be substituted for the GH3 sequence disclosed herein.

A further aspect of the present invention are transgenic plant cells, plant tissue and plants which have been genetically engineered to contain and express a nucleotide sequence encoding a cytokinin or auxin biosynthetic enzyme under the regulatory control of the tissue-specific transcription regulatory element, such that elevated gibberellin(s), auxin or cytokinin (as compared with normal plant tissue) are produced in the developing ovary or developing fruit and such that the fruit so produced is substantially seedless and is increased in solids content as compared with wildtype fruit. Preferably the tissue-specific transcription regulatory element is associated with the GH3 promoter and promoter-associated sequences (e.g., having the specifically exemplified nucleotide sequence given in SEQ ID NO:1) or the tissue-specific promoter is an AGL promoter (active in the ovaries of flowers), as exemplified by the sequence in SEQ ID NO:7.

The present invention provides a method for the production of substantially seedless fruit, said method comprising the steps of constructing an expression cassette in which a coding sequence for an auxin biosynthetic anzyme, cytokinin biosynthetic enzyme, or gibberellin biosynthetic enzyme (s) is operably linked to a transcriptional regulatory sequence which transcription regulatory sequence mediates the expression of a downstream coding sequence in a developing ovary and/or fruit, stably incorporating the expression cassette into a plant cell to produce a stably transformed plant cell and regenerating a transgenic plant from the stably transformed plant cell, whereby substantially seedless fruit having a higher solids content than wildtype fruit are produced when the transgenic plant is cultivated. The auxin biosynthetic coding sequence can be a tryptophan oxygenase coding sequence, for example, with an amino acid sequence as given in SEQ ID NO:3. The cytokinin biosynthetic coding sequence can be an isopentenyl transferase coding sequence, for example, having an amino acid sequence as given in SEQ ID NO:5.

The transcriptional regulatory sequence mediates tissue-specific expression of an operably linked downstream coding sequence in ovary and developing fruit tissue; the regulatory sequence can be an auxin-inducible transcriptional regulatory sequence, for example, the GH3 transcription regulatory sequences given in SEQ ID NO:1, the AGL5 transcriptional regulatory sequences as given in SEQ ID NO:7, 2A11, pTPRPF1, PLE36 or PZ130 transcription regulatory sequences.

The present invention further provides a transgenic plant which has been genetically engineered to contain and express an auxin biosynthetic enzyme coding sequence, a cytokinin biosynthetic enzyme coding sequence or gibberellin biosynthetic enzyme's coding sequence under the regulatory control of a tissue-specific transcription regulatory sequence which is selectively expressing in developing ovary tissue or developing fruit tissue. Seeds and embryos containing the genetically engineered DNA construct are within the intended definition of "plant," as are progeny containing the DNA construct. The auxin biosynthetic coding sequence can be a tryptophan oxygenase coding sequence, or the cytokinin biosynthetic coding sequence can be an isopentenyl transferase coding sequence. Transgenic plants described herein comprise a transcriptional regulatory sequence which mediates tissue-specific expression of an operably linked downstream coding sequence. The tissue specific regulatory sequence can be an auxin-inducible transcriptional regulatory sequence including, but not limited to, the GH3 sequences as given in SEQ ID NO:1. The transgenic plant producing substantially seedless fruit (e.g., in the absence of pollination) can be a dicotyledonous plant or a monocotyledonous plant. Such a dicotyledonous plant can be a member of the Solanaceae, including but not limited to, *Lycopersicon esculentum*, or it can be cucumber, watermelon, tobacco, apple, citrus, pear, fig, currant, muskmelon, squash, cherry, sweet potato, grapes, sugar beet, tea, strawberry, blackberry, blueberry, raspberry, loganberry, rose, chrysanthemum, sweet pepper, eggplant, among others. Substantially seedless cotton can also be produced according to the present invention.

Also provided by the present invention is an expression cassette comprising a coding sequence for an auxin, cytokinin or gibberellin biosynthetic enzyme and a transcription regulatory sequence operably linked thereto, which transcription regulatory sequence mediates the preferential expression of the downstream coding sequence in ovary or developing fruit. The auxin biosynthetic enzyme can be tryptophan oxygenase (also called tryptophan dioxygenase) and the cytokinin biosynthetic enzyme can be isopentenyl transferase. The transcriptional regulatory sequence can be any transcriptional regulatory sequence which specifically mediates gene expression in ovary and/or developing fruit.

DETAILED DESCRIPTION OF THE INVENTION

Figure 1:
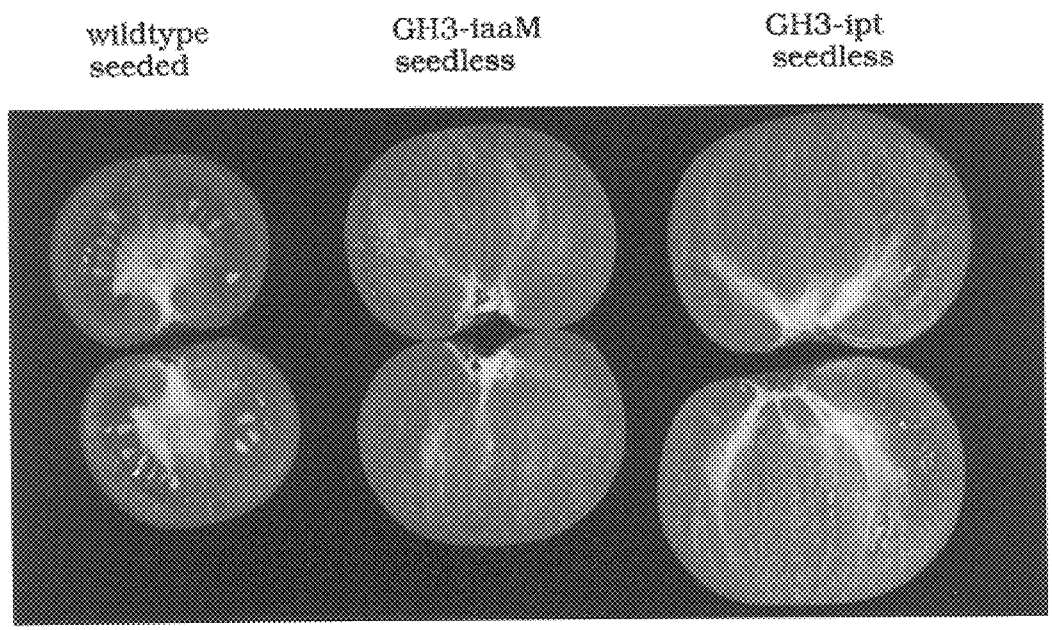
FIG. 1 is a photograph of representative wildtype seeded, seedless GH3-iaaM and seedless GH3-ipt fruits, each of which has been longitudinally sectioned for the photograph.

The following definitions are given in order to provide clarity as to the intent or scope of their usage in the specification and claims.

A non-naturally occurring recombinant nucleic acid molecule, e.g., a recombinant DNA molecule, is one which does not occur in nature; i.e., it is produced either by natural processes using methods known to the art, but is directed by man to produce a desired result or it has been artificially produced from parts derived from heterologous sources, i.e., a DNA construct, which parts may be naturally occurring or chemically synthesized molecules or portions thereof, and wherein those parts have been joined by ligation or other means known to the art.

A transgenic plant is one which has been genetically modified to contain and express heterologous DNA sequences, either as regulatory RNA molecules or as proteins. As specifically exemplified herein, a transgenic plant is genetically modified to contain and express a heterologous DNA sequence operably linked to and under the regulatory control of transcriptional control sequences by which it is not normally regulated, i.e., under the regulatory control of the tissue-specific transcriptional control sequences of the GH3 gene, for example, of *Glycine max* or of the AGL5 or PLE36 genes. Other tissue-specific regulatory sequences which mediate expression of an operably linked coding sequence in the developing ovary and in developing fruit can be used in place of the GH3 regulatory sequence. The present invention provides for the expression of a nucleotide sequence encoding an auxin biosynthetic enzyme or a cytokinin biosynthetic enzyme expressed under the regulatory control of transcription regulatory sequences expressed in the developing ovary and/or developing fruit of a plant. As specifically exemplified, the regulatory sequences are those of the GH3 gene of *Glycine max*. As used herein, a transgenic plant also refers to those progeny of the initial transgenic plant which carry and are capable of expressing the heterologous coding sequence under the regulatory control of the qualitative and/or quantitative transcription control sequences described herein. Seeds containing transgenic embryos are encompassed within this definition. In the context of the present application, it is understood that the expression cassette is stably maintained in the genome of a transformed host plant cell, plant tissue and/or plant. Because seed formation occurs when flowers of a transgenic plant of the present invention are pollinated, the ordinarily skilled artisan can readily reproduce the plants of the invention.

The term transgenic plant, as used herein, refers to a plant which has been genetically modified to contain and express heterologous DNA. As specifically exemplified herein, a transgenic plant is genetically modified to stably contain and consistently express (at the appropriate time) a seedless phenotype that is not normally present in the plant. As further used herein, a transgenic plant also refers to progeny of the initial transgenic plant, which progeny carry and are capable of expressing the seedless phenotype. Seeds containing transgenic embryo are encompassed within this definition. As used herein, a transgenic plant is a monocotyledonous or a dicotyledonous plant. Transgenic plants of the present invention can include, without limitation, tobacco, tomato, cucumber, cotton, grapes, tea, strawberry, rose, sweet pepper, hot pepper, eggplant, apple, citrus, pear, fig, currant, squash, watermelon, musk melon, sweet potato, blackberry, blueberry, raspberry, loganberry, other berries, chrysanthemum, among others. Transgenic plant cells and transgenic plant tissue are similarly genetically modified to stably contain heterologous DNA. Transgenic seeds and transgenic embryos are those which contain a specifically regulated DNA construct of the present invention.

A fruit, as used herein, is the structure which surrounds an ovule(s) of a plant. The methods and expression cassettes of the present invention are suited for producing substantially seedless fruits in the tomato, pepper, eggplant, cotton, cucumber, watermelon, raspberry, strawberry, blackberry, apple, citrus, pearl, fig, currant, muskmelon, squash, cherry, among others.

A seedless fruit, as used herein, is one which is substantially seedless. Substantially seedless means that there are from 0% to less than about 5% of the normal number of seeds produced per flower, under conditions which are not dependent on pollination. As specifically applied to tomatoes, (substantially) seedless fruits are those with 5 or fewer seeds per fruit. The seedless fruits of the present invention, surprisingly, exhibit an increased solids content as compared with wildtype fruit.

ipt is the mnemonic for the isopentenyl transferase gene, which functions in the biosynthesis of the cytokinin isopentenyladenosine. Plants genetically engineered to contain and express a heterologous ipt gene contained cytokinin levels about ten-fold greater than normal [Li et al. (1992) *Devel. Biol.* 153:386–395; Li et al. (1994) *Plant Science* 100:9–14]. As specifically exemplified herein, ipt is from *Agrobacterium tumefaciens*; the nucleotide and deduced amino acid sequences are given in SEQ ID NOs: 4 and 5, respectively.

iaaM is the mnemonic for the tryptophan oxygenase gene, which is in the biosynthetic pathway for the biosynthesis of the auxin indoleacetic acid. As specifically exemplified, the iaaM gene is from *Agrobacterium tumefaciens* for nucleotide and amino acid sequences, see SEQ ID Nos: 2 and 3.

While the present application specifically exemplifies iaaM and ipt from *A. tumefaciens*, it is understood by one of ordinary skill in the art that the exemplified iaaM can be replaced by any other plant or bacterial gene whose expression results in elevated auxin (IAA) levels. Suitable replacements include, but are not limited to, iaaH (from *A. tumefaciens* or iaaH or iaaM a plant pathogenic pseudomonad) to elevate auxin production. When operably linked to an appropriate tissue specific transcription regulator/promoter. Suitable replacements for the exemplified ipt sequences for increasing cytokinin levels are also within the skill in the art.

It is readily understood in the art what procedural modifications are necessary when such substitutions are made. Similarly, any transcription regulatory sequences can replace GH3, provided that an operably linked downstream coding sequence is preferentially or exclusively expressed in the ovary and/or developing fruit. Alternative suitable transcription regulatory sequences include those from genes including, but not limited to, AGL (AGL5 of *Arabidopsis thaliana*) [Savidge et al. 1995 *Plant Cell* 7:721–733], 2A11 [Pear et al. (1989) *Plant Molec. Biol.* 13:639–651], pTPRPF1 from tomato [Salts et al. (1991) *Plant Molec. Biol.* 17:149–150] and the ovary-specific transcription regulatory sequences from PLE36 from tobacco. The tobacco PLE36 gene is identified by the partial sequence as given in SEQ ID NO:6. The ovary-specific transcription regulatory sequence (in pZ130) from tomato is described in U.S. Pat. No. 5,175,095. Several gibberellin biosynthetic genes [Chiang, et al., (1995) *Plant Cell.* 7:195–201; Sun and Kamiya, (1994) *Plant Cell* 6:1509–1518; Xu, et al., (1995) *Proc. Natl. Acad. Sci. USA* 92:6640–6644]; or genes involved in gibberellin response [Jacobsen et al. (1996), *Proc. Natl. Acad. Sci. USA.* 93:9292–9296] in flowers and developing fruits are known. Regulated expression of these genes in ovary and/or developing fruit (using tissue specific transcription regulatory sequences as described herein) allows the development of substantially seedless fruit or substantially seedless cotton.

Production of seedless cotton fruits in transgenic cotton according to the methods of the present invention improves fiber productivity.

The present invention allows the production of seedless fruits without the expense of application of giberellin(s), auxin or cytokinin to unfertilized flowers or developing fruit, obviating the need for chemicals in the production setting. An added advantage of the present method is that it circumvents the need for pollination for fruit set, thus improving the efficiency of fruit production. It has been recognized that poor pollination is a major cause of incomplete fruit set and undersized fruit in the greenhouse and in field production of tomatoes, for example. In addition, the present transgenic methods circumvent any problems associated with uptake of an gibberellin(s), exogenous auxin or cytokinin and transport from a surface to which the exogenous growth regulator has been applied to the developing ovary or fruit.

The present inventor has produced transgenic tomato plants which produce elevated levels of plant hormones such as auxin (e.g., via a GH3 promoter driving expression of an tryptophan oxygenase coding sequence, GH3-iaaM) and cytokinin (e.g., via GH3-regulated expression of an isopentenyl transferase coding sequence, GH3-ipt) in ovary and developing fruits. The seedless fruits produced by these transgenic tomato plants produced seedless fruits which are significantly larger than wildtype seedless fruits and which, surprisingly, were significantly higher in solids content than wildtype fruits. With normal pollination tomato fruits from the transgenic plants express the GH3-ipt construct also show an increase in size when compared to wildtype seeded fruits.

TABLE 1

Comparison of Seedless and Wildtype Tomatoes

| Plant | Average Fruit Weight (% of their wildtype seeded fruits)* |
|---|---|
| Seedless fruits (less than 5 seeds per fruit) | |
| wildtype | 23% ± 16% |
| GH3-iaaM (auxin overproduction) | 108% ± 18% |
| GH3-ipt (cytokinin overproduction) | 117% ± 25% |
| Seeded fruits | |
| wildtype | 100% ± 17% |
| GH3-iaaM (auxin overproduction) | 138% ± 18% |
| GH3-ipt (cytokinin overproduction) | 144% ± 21% |

*Thirty to sixty tomato fruits produced from 5 to 10 plants were analyzed for each group.

Figure 2:
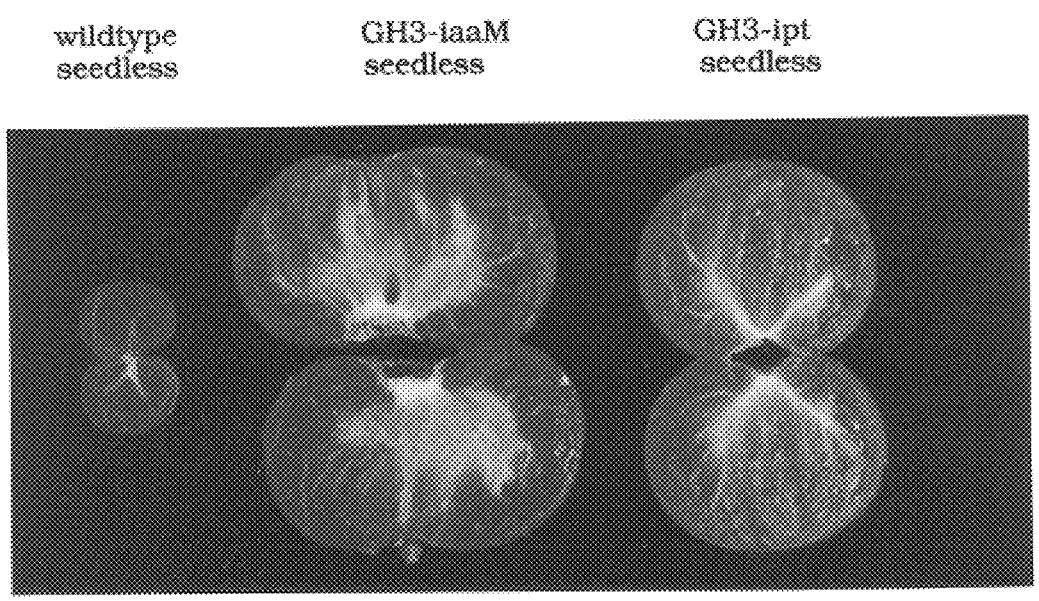
FIG. 2 is a photograph of representative wildtype seedless, seedless GH3-iaaM and seedless GH3-ipt fruits, each of which has halved along the longitudinal axis.

When grown in the greenhouse environment, T2 transgenic plants expressing either the GH3-iaaM or the GH3-ipt expression cassettes are morphologically indistinguishable from wildtype plants. However, the transgenic fruits are significantly larger than the wildtype fruits. Representative wildtype seeded, seedless GH3-iaaM and seedless GH3-ipt fruits are shown in FIGS. 1 and 2.

In contrast to unpollinated wildtype fruits, the transgenic fruits of the present invention can grow and develop into normal sized or larger fruits. Studies of these tomatoes have shown that the ripe transgenic tomatoes of the present invention have increased solid content than wildtype fruits, and the taste of the transgenic fruits is not different from the taste of the wildtype fruit. In addition, fruit production according to the present invention is not dependent on pollination, which, in a greenhouse setting, may be poor and/or dependent on mechanical pollination.

By weighing tomatoes before and after freeze-drying, the solids contents of the GH3 promoter-iaaM seedless tomato fruits and the corresponding wildtype seeded fruits were determined. The seedless fruits produced from the GH3 promoter-iaaM tomato plants contain 50–110% more solids (dry matter) than the wildtype seeded fruits (see Table 2). Because yield and quality of tomato fruits and their products depend on contents of solids and the composition of the raw materials in fruits, the seedless tomatoes of the present invention are highly desirable for the tomato processing industry.

TABLE 2

Solids Contents of Tomato Fruits

| Fruit type | Solids contents |
|---|---|
| money maker wildtype seeded fruits (25 fruits determined): | 100%* |
| money maker GH3 promoter-iaaM seedless fruits | |
| Fruits from Transgenic Plant 1 (5 fruits determined): | 178% |
| Fruits from Transgenic Plant 2 (9 fruits determined): | 212% |
| Fruits from Transgenic Plant 3 (7 fruits determined): | 183% |
| Fruits from Transgenic Plant 3 (3 fruits determined): | 203% |
| money maker GH3 promoter-ipt seedless fruits | |
| Fruits from Transgenic Plant 1 (6 fruits determined): | 158% |
| Fruits from Transgenic Plant 2 (4 fruits determined): | 173% |
| Fruits from Transgenic Plant 3 (8 fruits determined): | 191% |

*Because we compared solids contents of the GH3 promoter-iaaM or GH3 promoter-ipt seedless fruits to those of the wildtype seeded fruits, the solids contents of the wildtype seeded fruits were designated as 100%.

Promoters which are known or are found to cause transcription in plant cells can be used in the present invention. As described below, it is preferred that the particular promoter selected should be selectively expressed in developing fruit or ovary and capable of causing sufficient expression of a cytokinin biosynthetic gene or an auxin biosynthetic gene or a gibberellin biosynthetic gene to result in the production of a substantially seedless fruit in the absence of pollination. This is because an effective amount of auxin, gibberellin, or cytokinin in the ovary or developing fruit can stimulate fruit growth and development without formation of seeds. Seeds are source of endogenous auxin and cytokinin in developing fruits. The amount of auxin, cytokinin, and gibberellin(s) needed to induce fruit growth development in the absence of pollination may vary with the type of plant, and appropriate modulation of the expression of the corresponding gene is well within skill in the art.

The promoters used in the DNA constructs of the present invention may be modified, if desired, to affect their control characteristics. For purposes of this invention, the phrase "promoter" thus includes variations of the promoter, e.g., promoters derived by means of ligation with operator regions, random or controlled mutagenesis as well as tandem of multiple copies of enhancer elements, etc.

The use of an organ-specific promoter is contemplated by the invention. Preferably, the expression of a downstream coding sequence occurs in a tissue specific and developmental stage specific manner. It is preferred that the promoter driving the expression of the gibberellin, auxin or cytokinin biosynthetic gene is selectively expressed in the desired tissue and at the stage of development effective for inducing fruit growth and development.

A coding sequence used in a DNA construct of this invention may be modified, if desired, to create mutants, either by random or controlled mutagenesis, using methods known to those skilled in the art. Those mutants can include synonymous coding sequences which have been modified to optimize the level of expression in a particular host cell, to create or remove restriction endonuclease recognition sites or to otherwise facilitate or accommodate molecular biological manipulations according to the knowledge of one of ordinary skill in the art. Such mutants and variants are therefore within the scope of the present invention.

The 3' non-translated region contains a polyadenylation signal which functions to cause the addition of polyadenylate nucleotides to the 3' end of the RNA. Examples of suitable 3' regions are (1) the 3' transcribed, non-translated regions containing the polyadenylation signal of the tumor-inducing (Ti) plasmid genes of Agrobacterium, such as the nopaline synthase (NOS) gene, and (2) plant genes like the 7S soybean storage protein genes and the pea E9 small subunit of the RuBP carboxylase gene.

The mRNA produced by a DNA construct of the present invention also contains a 5' non-translated leader sequence.

This sequence can be derived from the promoter selected to express the gene, and can be specifically modified so as to increase translation of the mRNA. The 5' non-translated regions can be obtained from viral RNAs, from suitable eukaryotic genes, or may be synthesized. The present invention is not limited to constructs, as presented in the following examples, wherein the non-translated region is derived from the 5' non-translated sequence that accompanies the promoter sequence. Rather, the non-translated leader sequence can be part of the 5' end of the non-translated region of the native coding sequence for the dsRNA-binding protein, or part of the promoter sequence, or can be derived from an unrelated promoter or coding sequence as discussed above.

While in most cases the heterologous DNA which is inserted into plant cells contains a gene which encodes a selectable marker such as an antibiotic resistance marker (e.g., the kanamycin/neomycin resistance determinant), this is not mandatory.

A DNA construct of the present invention can be inserted into the genome of a plant or animal by any suitable method. Such methods may involve, for example, the use of liposomes, electroporation, diffusion, particle bombardment, microinjection, gene gun, chemicals that increase free DNA uptake, e.g., calcium phosphate coprecipitation, viral vectors, and other techniques practiced in the art.

Suitable plant transformation vectors include those derived from a Ti plasmid of *Agrobacterium tumefaciens*, such as those disclosed by Herrera-Estrella (1983), Bevan (1983), Klee (1985) and EPO publication 120,516 (Schilperoort et al.). In addition to plant transformation vectors derived from the Ti or root-inducing (Ri) plasmids of Agrobacterium, alternative methods can be used to insert the DNA constructs of this invention into plant cells.

A DNA construct prepared in accordance with the present invention is preferably introduced, via a suitable vector as described above, into cells or protoplasts derived from agriculturally important crops, e.g., dicotyledonous plants such as tobacco, tomato, cotton, watermelon, cucumber, strawberry, rose, sweet pepper, hot pepper, eggplant, apple, citrus, pear, fig, currant, squash, musk melon, sweet potato, blackberry, blueberry, raspberry, loganberry, other berries, chrysanthemum, among others, or monocotyledonous plants such as the grasses or lilies.

The choice of vector in which the expression cassette of the present invention is operatively linked depends directly, as is well known in the art, on the functional properties desired, e.g., replication, protein expression, and the host cell to be transformed, these being limitations inherent in the art of constructing recombinant DNA molecules. In preferred embodiments, the vector utilized includes a prokaryotic replicon, i.e., a DNA sequence having the ability to direct autonomous replication and maintenance of the recombinant DNA molecule extra-chromosomally when introduced into a prokaryotic host cell, such as a bacterial host cell. Such replicons are well known in the art. In addition, preferred embodiments that include a prokaryotic replicon also include a gene whose expression confers a selective advantage, such as a drug resistance, to the bacterial host cell when introduced into those transformed cells. Typical bacterial drug resistance genes are those that confer resistance to ampicillin or tetracycline, among other selective agents. The neomycin phosphotransferase gene has the advantage that it is expressed in eukaryotic as well as prokaryotic cells.

Those vectors that include a prokaryotic replicon also typically include convenient restriction sites for insertion of a recombinant DNA molecule of the present invention. Typical of such vector plasmids are pUC8, pUC9, pBR322, and pBR329 available from BioRad Laboratories (Richmond, Calif.) and pPL, pK and K223 available from Pharmacia (Piscataway, N.J.), and pBLUESCRIPT and pBS available from Stratagene (La Jolla, Calif.). A vector of the present invention may also be a Lambda phage vector including those Lambda vectors described in *Molecular Cloning: A Laboratory Manual*, Second Edition, Maniatis et al., eds., Cold Spring Harbor, N.Y. (1989) and the Lambda ZAP vectors available from Stratagene (La Jolla, Calif.). Other exemplary vectors include pCMU [Nilsson et al. (1989) Cell 58:707]. Other appropriate vectors may also be synthesized, according to known methods; for example, vectors pCMU/$K^b$ and pCMUII used in various applications herein are modifications of pCMUIV (Nilson et al., supra).

Typical expression vectors capable of expressing a recombinant nucleic acid sequence in plant cells and capable of directing stable integration within the host plant cell include vectors derived from the tumor-inducing (Ti) plasmid of *Agrobacterium tumefaciens* described by Rogers et al. (1987) Meth. in Enzymol. 153:253–277, and several other expression vector systems known to function in plants. See for example, Verma et al., Published PCT Application No. WO87/00551; Cocking and Davey Science (1987) 236:1259–1262.

In preferred embodiments, the plant cell expression vectors used include a selection marker that is effective in a eukaryotic cell, preferably a drug resistance selection marker. In preferred embodiments where a recombinant nucleic acid molecule of the present invention is expressed in plant cells, a preferred drug resistance marker is the gene whose expression results in kanamycin resistance, i.e., the chimeric gene containing nopaline synthetase promoter, Tn5 neomycin phosphotransferase II and nopaline synthetase 3' non-translated region described by Rogers et al., *Methods for Plant Molecular Biology*, A. Weissbach and H. Weissbach, eds., Academic Press, Inc., San Diego, Calif. (1988).

A transgenic plant can be produced by any means known to the art, including but not limited to *Agrobacterium tumefaciens*-mediated DNA transfer, preferably with a disarmed T-DNA vector, electroporation, direct DNA transfer, and particle bombardment (See Davey et al. (1989) *Plant Mol. Biol.* 13:275; Walden and Schell (1990) *Eur. J. Biochem.* 192:563; Joersbo and Burnstedt (1991) *Physiol. Plant.* 81:256; Potrykus (1991) *Annu. Rev. Plant Physiol. Plant Mol. Biol.* 42:205, Gasser and Fraley (1989) *Science* 244:1293; Leemans (1993) *Bio/Technology.* 11:522; Beck et al. (1993) *Bio/Technology.* 11:1524; Koziel et al. (1993) *Bio/Technology.* 11:194; and Vasil et al. (1993) *Bio/Technology.* 11:1533.). Techniques are well-known to the art for the introduction of DNA into monocots as well as dicots, as are the techniques for culturing such plant tissues and regenerating those tissues. Monocots which have been successfully transformed and regenerated include wheat, corn, rye, rice and asparagus. For example, U.S. Pat. No. 5,350,689 (1994, Shillito et al.) describes transgenic *Zea mays* plants regenerated from protoplasts and protoplast-derived cells. For efficient production of transgenic plants, it is desired that the plant tissue used for transformation possess a high capacity for regeneration. Transgenic aspen tissue has been prepared and transgenic plants have been regenerated [Devellard et al. (1992) *C.R. Acad. Sci. Ser. VIE* 314:291–298K; Nilsson et al. (1992) *Transgenic Res.* 1:209–220; Tsai et al. (1994) *Plant Cell Rep.* 14:94–97]. Poplars have also been transformed [Wilde et al. (1992)

Plant Physiol. 98:114–120]. Technology is also available for the manipulation, transformation and regeneration of Gymnosperm plants in the laboratory. For example, U.S. Pat. No. 5,122,466 (1992, Stomp et al.) describes the ballistic transformation of conifers, with preferred target tissue being meristematic and cotyledon and hypocotyl tissues. U.S. Pat. No. 5,041,382 (1991, Gupta et al.) describes enrichment of conifer embryonal cells.

Techniques and agents for introducing and selecting for the presence of heterologous DNA in plant cells and/or tissue are well-known. Genetic markers allowing for the selection of heterologous DNA in plant cells are well-known, e.g., genes carrying resistance to an antibiotic such as kanamycin, hygromycin, gentamicin, or bleomycin. The marker allows for selection of successfully transformed plant cells growing in the medium containing the appropriate antibiotic because they will carry the corresponding resistance gene.

Other techniques for genetically engineering plant cells and/or tissue with an expression cassette comprising an inducible promoter or chimeric promoter fused to a heterologous coding sequence and a transcription termination sequence are to be introduced into the plant cell or tissue by Agrobacterium-mediated transformation, electroporation, microinjection, particle bombardment or other techniques known to the art. The expression cassette advantageously further contains a marker allowing selection of the heterologous DNA in the plant cell, e.g., a gene carrying resistance to an antibiotic such as kanamycin, hygromycin, gentamicin, or bleomycin.

The transcription regulatory sequences, particularly the tissue-specific transcription regulatory element (or the GH3, AGL5 or other ovary and/or developing fruit specific promoter with the inducible and preferably the transcription-enhancing element) is useful in controlling gene expression in transgenic plant cells in suspension cell culture as an alternative to expression in transgenic plants. It is understood that transgenic plants can be similarly used to express heterologous coding sequences as can transgenic plant cells.

Many of the procedures useful for practicing the present invention, whether or not described herein in detail, are well known to those skilled in the art of plant molecular biology. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol* 218, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DA Cloning* Vol. I and II, IRL Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1–4, Plenum Press, New York, Kaufman (1987) in *Genetic Engineering Principles and Methods*, J. K. Setlow, ed., Plenum Press, NY, pp. 155–198; Fitchen et al. (1993) *Annu. Rev. Microbiol.* 47:739–764; Tolstoshev et al. (1993) in *Genomic Research in Molecular Medicine and Virology*, Academic Press. Abbreviations and nomenclature, where employed, are deemed standard in the field and commonly used in professional journals such as those cited herein.

All references cited in the present application are incorporated by reference herein.

The following examples are provided for illustrative purposes, and are not intended to limit the scope of the invention as claimed herein. Any variations in the exemplified sequences and methods which occur to the skilled artisan are intended to fall within the scope of the present invention.

As used herein, the term "comprising" is intended in a nonlimiting sense.

EXAMPLES

Example 1

Production of GH3-iaaM and GH3-ipt Expression Cassettes

The GH3 promoter was cloned from soybean (*Glycine max*) as described by Hagen et al. (1991) *Plant Molec. Biol.* 17:567–579. The nucleotide sequence of the soybean GH3 promoter is given in SEQ ID NO:1. The GH3 promoter was cloned into pUC18 using EcoRI and NcoI.

The iaaM and ipt genes were cloned using polymerase chain reaction technology from *Agrobacterium tumefaciens* (pTich5). The coding sequences and deduced amino acid sequences are provided in SEQ ID NO:2–3 and 4–5, respectively. The product of the iaaM gene, tryptophan oxygenase, converts tryptophan to indoleacteamide. The int gene encodes isopentenyl transferase, an enzyme in the cytokinin biosynthetic pathway.

Figure 3:
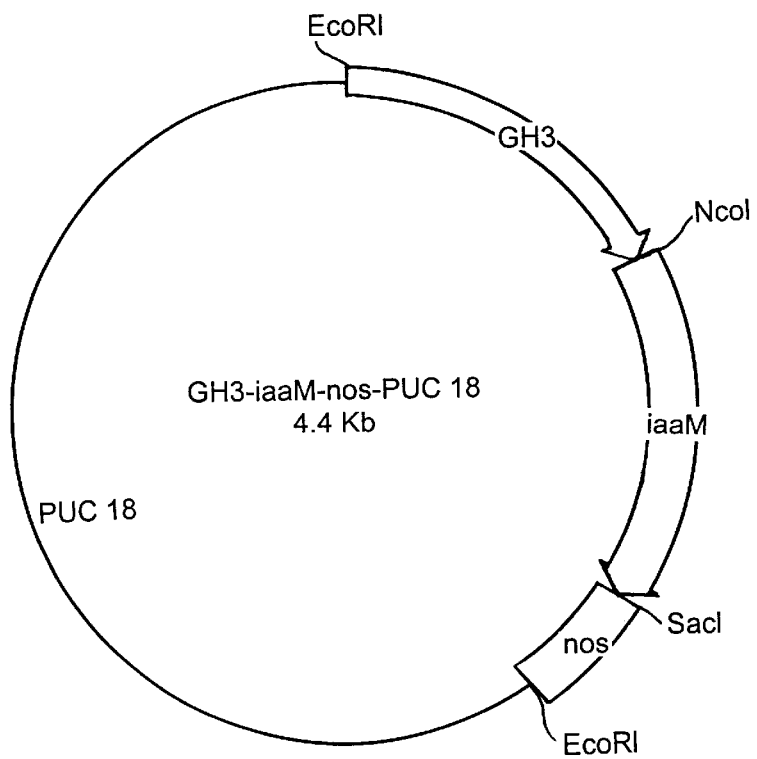
FIG. 3 illustrates a partial restriction map of the GH3-iaaM-NOS fusion gene cloned in pUC18.
Figure 4:
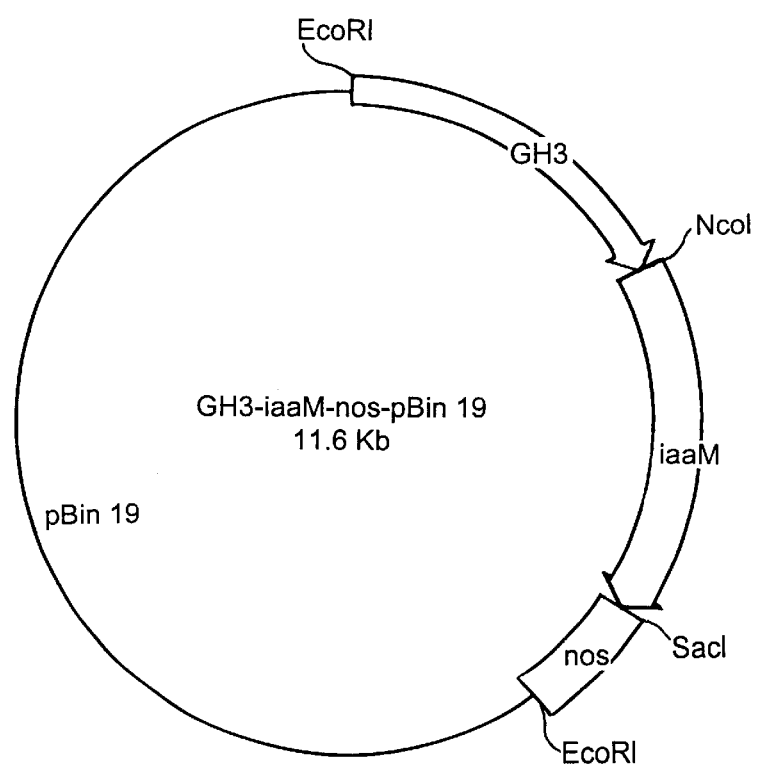
FIG. 4 is a diagram of the GH3-iaaM-NOS fusion gene as cloned into pBIN19.
Figure 5:
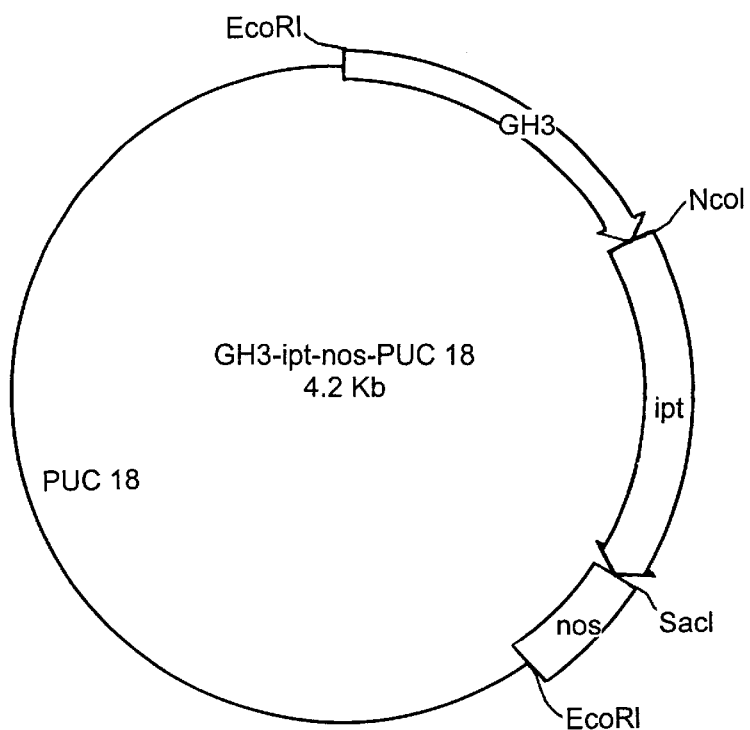
FIG. 5 illustrates relevant restriction endonuclease sites used in the construction of the GH3-ipt-NOS fusion gene in pUC18.
Figure 6:
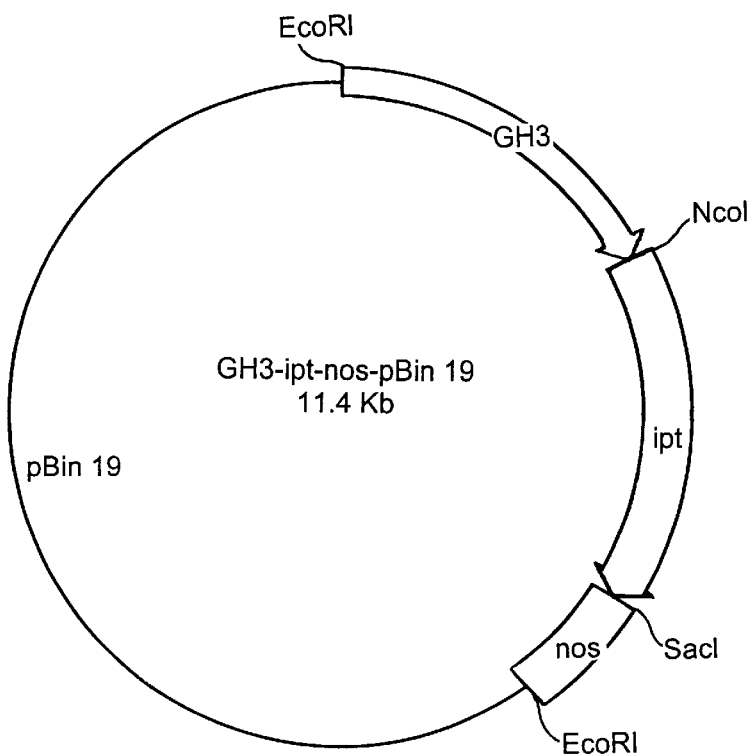
FIG. 6 is a diagram of the GH3-ipt-NOS fusion gene as inserted in pBIN19.

To make the expression cassettes of the present invention, the coding sequence of the iaaM or ipt gene was fused with the GH3 promoter sequences cloned in pUC18 at the NcoI and SacI sites. The 3' untranslated NOS gene sequence was purchased from Stratagene, La Jolla, Calif., and inserted. The "GH3 promoter-iaaM-3'-NOS" and "GH promoter-ipt-3'NOS" genes were then cut from the pUC19 using EcoRI and ligated into the EcoRI site of pBIN19 binary vector in separate experiments [Bevan, (1984) *Nucleic Acid Research* 12:8711–8721]. The pBIN19 containing the GH3-ipt or GH3-iaaM genes were mobilized into *Agrobacterium tumefaciens* strain LBA 4404 using *E. coli* harboring pRK2103 as a helper plasmid [Bevan (1984) supra; Ditta et al. (1980) *Proc. Natl. Acad. Sci.* 77:7347–7351]. See FIGS. 3 and 4 restriction maps of the GH33-iaaM-NOS sequences cloned in pUC18 and pBIN19, respectively. See FIGS. 5 and 6 for the GH3-ipt-NOS sequences cloned in pUC18 and pBIN19, respectively.

The AGL5 transcription regulatory sequences were similarly cloned and subcloned (See FIGS. 5–8).

Example 2

Production of Transgenic Tomato Plants

Tomato seeds were sterilized using 10% chlorox (5.3% sodium hypochlorite and germinated on MS medium solidified with 0.65% agar at 25° C., 16 hr. photoperiod with light intensity of 35 $mEm^2S\text{-}1$ for 5–7 days. Cotyledons of tomato seedlings were removed from young seedlings and wounded by cutting their ends off. The cotyledons were carefully placed on tobacco feeder layer plates upside down under light for 24 hours. *Agrobacterium tumefaciens* strain LBA4404 [Bevan (1984) supra] containing the GH3-iaaM or GH3-ipt expression cassettes were cultured for 2 to 3 days, then diluted and subcultured overnight. The cotyledons were removed from the feeder plates and incubated with the A. tumefaciens cultures for 20–30 minutes with occasional swirling. The inoculated cotyledons were then separately transferred to sterile paper filters to remove excess liquid, and placed on tobacco feeder plates upside down. After 48 hours of cocultivation at 25° C., the cotyledons were transferred onto a shoot regeneration medium containing kanamycin and zeatin. Shoots were formed from the infected edges of the cotyledons after 3–4 weeks. When the shoots were ready for rooting, they were separated from callus tissues and placed on rooting medium containing auxin (IBA). After each shoots reached a height of about 2 inches and had developed a nice root system, it was transferred to soil and placed in a greenhouse to produce seeds.

I claim:

1. A DNA construct comprising a first portion encoding an isopentenyl transferase or a tryptophan monooxygenase and a second portion which is a plant-expressible promoter which is specifically expressed in the ovary or developing fruit of a plant, said second portion being operably linked to the first portion, wherein said promoter is selected from the group consisting of an AGL promoter and a GH3 promoter, wherein expression of said construct in the ovary or developing fruit of a plant results in plants producing from 0% to less than about 5% of the number of seeds per flower as compared to a wild type plant, and wherein fruit produced by the plants is increased in solids content as compared with a wild type fruit.

2. The DNA construct of claim 1 wherein the plant-expressible promoter is the GH3 promoter having the nucleotide sequence as given in SEQ ID NO:1.

3. The DNA construct of claim 1 wherein the plant-expressible promoter is the AGL promoter having the nucleotide sequence as given in SEQ ID NO:7.

4. The DNA construct of claim 1 wherein the isopentenyl transferase has the amino acid sequence as given in SEQ ID NO:5.

5. The DNA construct of claim 1 wherein the tryptophan oxygenase has the amino acid sequence as given in SEQ ID NO:3.

6. The DNA construct of claim 2, wherein the first portion encodes isopentenyl transferase.

7. The DNA construct of claim 2, wherein the first portion encodes tryptophan monooxygenase.

8. The DNA construct of claim 3, wherein the first portion encodes isopentenyl transferase.

9. The DNA construct of claim 3, wherein the first portion encodes tryptophan monooxygenase.

10. A transgenic plant comprising the DNA construct of claim 1.

11. The transgenic plant of claim 10, wherein said plant is a dicotyledonous plant.

12. The transgenic plant of claim 10, wherein said dicotyledonous plant is a tomato, cucumber, watermelon, tobacco, apple, citrus, pear, fig, currant, muskmelon, squash, cherry, sweet potato, grape, sugar beet, tea, strawberry, blackberry, blueberry, raspberry, loganberry, rose, chrysanthemum, sweet pepper or eggplant plant.

13. The transgenic plant of claim 11 which is a tomato plant.

14. The transgenic plant of claim 11 which is a watermelon plant.

15. The transgenic plant of claim 11 which is a cucumber plant.

16. The transgenic plant of claim 10, wherein the plant produces 0% of the number of seeds per flower, compared with a wild type plant.

17. The transgenic plant of claim 10, wherein said first portion encodes isopentenyl transferase and said second portion is an AGL promoter, said AGL promoter having the nucleotide sequence set forth in SEQ ID NO:7.

18. The transgenic plant of claim 10, wherein said first portion encodes tryptophan monooxygenase and said second portion is an AGL promoter, said AGL promoter having the nucleotide sequence set forth in SEQ ID NO:7.

19. The transgenic plant of claim 10, wherein said first portion encodes isopentenyl transferase and said second portion is a GH3 promoter, said GH3 promoter having the nucleotide sequence set forth in SEQ ID NO:1.

20. The transgenic plant of claim 10, wherein said first portion encodes tryptophan monooxygenase and said second portion is a GH3 promoter, said GH3 promoter having the nucleotide sequence set forth in SEQ ID NO:1.

21. A transgenic seed or a transgenic embryo comprising the DNA construct of claim 1.

22. The transgenic seed or transgenic embryo of claim 21, which is a dicotyledonous seed or embryo.

23. The transgenic seed or transgenic embryo of claim 22, wherein said dicotyledonous seed or embryo is a tomato, cucumber, watermelon, tobacco, apple, citrus, pear, fig, currant, muskmelon, squash, cherry, sweet potato, grape, sugar beet, tea, strawberry, blackberry, blueberry, raspberry, loganberry, rose, chrysanthemum, sweet pepper or eggplant seed or embryo.

24. The transgenic seed or transgenic embryo of claim 22 which is a tomato seed or embryo.

25. The transgenic seed or transgenic embryo of claim 22 which is a watermelon seed or embryo.

26. The transgenic seed or transgenic embryo of claim 22 which is a cucumber seed or embryo.

27. A method for producing a transgenic plant producing from 0% to less than about 5% of the number of seeds per flower, compared to a wild type plant, and wherein fruit produced by the transgenic plant is increased in solids content as compared with a wild type fruit, said method comprising the steps of:

(a) introducing into a plant cell or plant tissue a DNA construct comprising a first portion encoding an isopentenyl transferase or a tryptophan monooxygenase and a second portion which is a plant-expressible promoter specifically expressed in ovary or in developing fruit in a plant, wherein said promoter is selected from the group consisting of an AGL promoter and a GH3 promoter, said promoter being operably linked to the first portion to produce a transformed plant cell or a transformed plant tissue, and (b) regenerating a transgenic plant from the transformed plant cell or transformed plant tissue of step (a), whereby the transgenic plant produces from 0% to less than about 5% of the number of seeds per flower as compared to a wild type plant, and wherein fruit of the transgenic plant is increased in solids content as compared with a wild type fruit.

28. The method of claim 27 wherein the first portion encodes an isopentenyl transferase and wherein the promoter is the GH3 promoter.

29. The method of claim 27 wherein the first portion encodes a tryptophan oxygenase and wherein the promoter is the GH3 promoter.

30. The method of claim 27 wherein the first portion encodes an isopentenyl transferase and wherein the promoter is the AGL promoter.

31. The method of claim 27 wherein the first portion encodes a tryptophan oxygenase and wherein the promoter is the AGL promoter.

32. The method of claim 27 wherein said plant is a dicotyledonous plant.

33. The method of claim 32 wherein said dicotyledonous plant is a tomato, cucumber, watermelon, tobacco, apple, citrus, pear, fig, currant, muskmelon, squash, cherry, sweet If potato, grape, sugar beet, tea, strawberry, blackberry, blueberry, raspberry, loganberry, rose, chrysanthemum, sweet pepper or eggplant plant.

34. The method of claim 32, wherein said plant is a tomato plant.

35. The method of claim 32, wherein said plant is a watermelon plant.

36. The method of claim 32, wherein said plant is a cucumber plant.

37. The method of claim 27, wherein. said first portion encodes isopentenyl transferase and said second portion is an AGL promoter, said AGL promoter having the nucleotide sequence set forth in SEQ ID NO:7.

38. The method of claim 27, wherein. said first portion encodes tryptophan monooxygenase and said second portion is an AGL promoter, said AGL promoter having the nucleotide sequence set forth in SEQ ID NO:7.

39. The method of claim 27, wherein. said first portion encodes isopentenyl transferase and said second portion is a GH3 promoter, said GH3 promoter having the nucleotide sequence set forth in SEQ ID NO:1.

40. The method of claim 27, wherein. said first portion encodes tryptophan monooxygenase and said second portion is a GH3 promoter, said GH3 promoter having the nucleotide sequence set forth in SEQ ID NO:1.

* * * * *

UNITED STATES PATENT AND TRADEMARK OFFICE
CERTIFICATE OF CORRECTION

PATENT NO.    : 6,268,552 B1
DATED         : July 31, 2001
INVENTOR(S)   : Li

Figure 7:
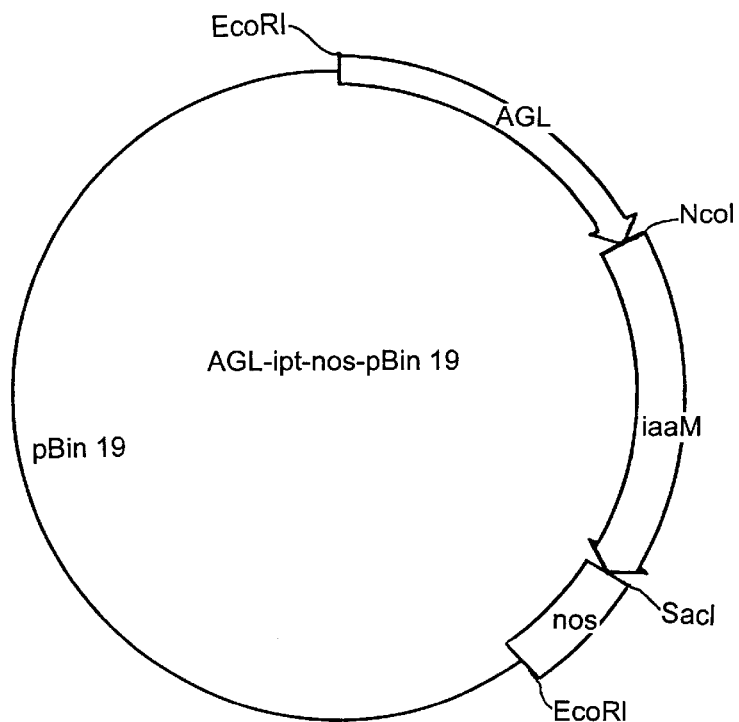
FIG. 7 is a diagram of the AGL5-iaaM-NOS fusion gene as inserted in pBIN19.
Figure 8:
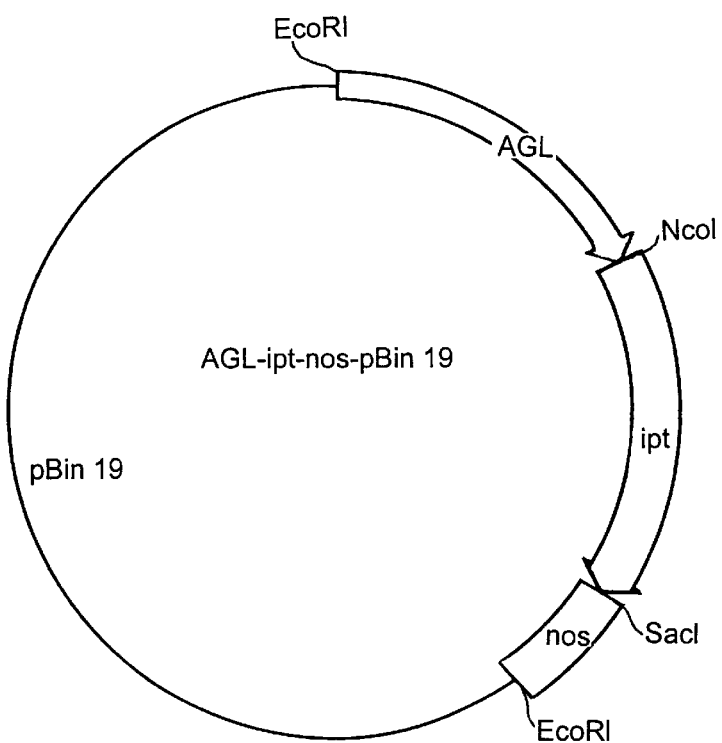
FIG. 8 is a diagram of the AGL5-ipt-NOS fusion gene as inserted in pBIN19.

It is certified that error appears in the above-identified patent and that said Letters Patent is hereby corrected as shown below:

Drawings,
In Fig. 7, rewrite "AGL-ipt-nos-pBin 19" as -- AGL-iaaM-nos-pBin 19 --.

Column 2,
Line 21, insert "that" after "cassette".

Column 3,
Line 58, delete "dioxygenase" and replace with -- monooxygenase --.

Column 5,
Line 63, insert "from" after -- iaaM --.
Line 64, rewrite "production. When" as -- production when --.

Column 12,
Line 31, delete "int" and replace with -- ipt --.
Line 48, delete "GH33" and replace with -- GH3 --.

Signed and Sealed this

Second Day of April, 2002

Attest:

JAMES E. ROGAN
*Attesting Officer*   *Director of the United States Patent and Trademark Office*

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 749 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
GAATTCACGA ATAAAGAAAA ATTAAAAGTC TCAACAAATG TAGTAAGAGG GCAAAAATAG      60

GCTGTAATAA CTTGCAAAGT GTGCAGTGAA GTTTTCTTCG TACTACGTAG AAACTTCTCA     120

GTTCTTTCTC ACATTTCTGC CCACAGGGAT TTGGATTTCG TGTATTGACG CAGTTATACC     180

ATCATTAATC TTATCCTTCA ATTTTTATAA AATTAATAAA ATAAATAAAA AATTAATTAA     240

GCTTCCGATC TTGACTGCCT GCTTGAATGC GTCGGCGGCG CCCATTAGTT TCTCATGCCA     300

ACACACCCTA TAACGCCTAA TTTTGCCCGA GTATTACTAT ATTGGGAGAA CTTTTGCTGA     360

CGTGGCGACA CATCTGGACC CACATGTCGG CCACCATGCA CCATCCCTGG CCCTCGTGTC     420

TCCTCAATAA GCTACACAAT TTGAAACATA CACGCAATCC TTTGTCTCAA TAAGTTCCAC     480

TCAGGTACTG TTTTCTCCCG CAACCATGAC GTAATTCTGT AAATCACATG TTTCATGCTC     540

CCAATTATTT TCCGCTTCTA TAAATACCTC TCCCATTTCG CAACTTTTCT CCATCCATAC     600

TCATCCACTT CTTGAACCGT GCCTTAACTA AACTAGAGCT AGAATTAGAG TTAGCTACCT     660

TGCCTAATTC ACAAACGCGT CCCTCTACGG CTCTACCTAT TAGCTATCTT TTTTGTGCTG     720

TGATTGAAAT TAATTTGTGA TAGCTCACC                                      749
```

(2) INFORMATION FOR SEQ ID NO:2:

(i) SEQUENCE CHARACTERISTICS:
      (A) LENGTH: 2211 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION: 4..2205

-continued (xi) SEQUENCE DESCRIPTION: SEQ ID NO:2:

```
ACA ATG GTC GAT AAG GCG GAT GAA TTG GAC CGC AGG GTT TCC GAT GCC        48
    Met Val Asp Lys Ala Asp Glu Leu Asp Arg Arg Val Ser Asp Ala
      1               5                  10                  15

TTC TTA GAA CGA GAA GCT TCT AGG GGA AGG AGG ATT ACT CAA ATC TCC        96
Phe Leu Glu Arg Glu Ala Ser Arg Gly Arg Arg Ile Thr Gln Ile Ser
                    20                  25                  30

ACC GAG TGC AGC GCT GGG TTA GCT TGC AAA AGG CTG GCC GAT GGT CGC       144
Thr Glu Cys Ser Ala Gly Leu Ala Cys Lys Arg Leu Ala Asp Gly Arg
                35                  40                  45

TTC CCC GAG ATC TCA GCT GGT GGA AAG GTA GCA GTT CTC TCC GCT TAT       192
Phe Pro Glu Ile Ser Ala Gly Gly Lys Val Ala Val Leu Ser Ala Tyr
             50                  55                  60

ATC TAT ATT GGC AAA GAA ATT CTG GGG CGG ATA CTT GAA TCG AAA CCT       240
Ile Tyr Ile Gly Lys Glu Ile Leu Gly Arg Ile Leu Glu Ser Lys Pro
 65                  70                  75

TGG GCG CGG GCA ACA GTG AGT GGT CTC GTT GCC ATC GAC TTG GCA CCA       288
Trp Ala Arg Ala Thr Val Ser Gly Leu Val Ala Ile Asp Leu Ala Pro
 80                  85                  90                  95

TTT TGC ATG GAT TTC TCC GAA GCA CAA CTA ATC CAA GCC CTG TTT TTG       336
Phe Cys Met Asp Phe Ser Glu Ala Gln Leu Ile Gln Ala Leu Phe Leu
                    100                 105                 110

CTG AGC GGT AAA AGA TGT GCA CCG ATT GAT CTT AGT CAT TTC GTG GCC       384
Leu Ser Gly Lys Arg Cys Ala Pro Ile Asp Leu Ser His Phe Val Ala
                115                 120                 125

ATT TCA ATC TCT AAG ACT GCC GGC TTT CGA ACC CTG CCA ATG CCG CTG       432
Ile Ser Ile Ser Lys Thr Ala Gly Phe Arg Thr Leu Pro Met Pro Leu
            130                 135                 140

TAC GAG AAT GGC ACG ATG AAA TGC GTT ACC GGG TTT ACC ATA ACC CTT       480
Tyr Glu Asn Gly Thr Met Lys Cys Val Thr Gly Phe Thr Ile Thr Leu
145                 150                 155

GAA GGG GCC GTG CCA TTT GAC ATG GTA GCT TAT GGT CGA AAC CTG ATG       528
Glu Gly Ala Val Pro Phe Asp Met Val Ala Tyr Gly Arg Asn Leu Met
160                 165                 170                 175

CTG AAG GGT TCG GCA GGT TCC TTT CCA ACA ATC GAC TTG CTC TAC GAC       576
Leu Lys Gly Ser Ala Gly Ser Phe Pro Thr Ile Asp Leu Leu Tyr Asp
                180                 185                 190

TAC AGA CCG TTT TTT GAC CAA TGT TCC GAT AGT GGA CGG ATC GGC TTC       624
Tyr Arg Pro Phe Phe Asp Gln Cys Ser Asp Ser Gly Arg Ile Gly Phe
                195                 200                 205

TTT CCG GAG GAT GTT CCT AAG CCG AAA GTG GCG GTC ATT GGC GCT GGC       672
Phe Pro Glu Asp Val Pro Lys Pro Lys Val Ala Val Ile Gly Ala Gly
            210                 215                 220

ATT TCC GGA CTC GTG GTG GCA AAC GAA CTG CTT CAT GCT GGG GTA GAC       720
Ile Ser Gly Leu Val Val Ala Asn Glu Leu Leu His Ala Gly Val Asp
225                 230                 235

GAT GTT ACA ATA TAT GAA GCA AGT GAT CGT GTT GGA GGC AAG CTT TGG       768
Asp Val Thr Ile Tyr Glu Ala Ser Asp Arg Val Gly Gly Lys Leu Trp
240                 245                 250                 255

TCA CAT GCT TTC AGG GAC GCT CCT AGT GTC GTG GCC GAA ATG GGG GCG       816
Ser His Ala Phe Arg Asp Ala Pro Ser Val Val Ala Glu Met Gly Ala
                260                 265                 270

ATG CGA TTT CCT CCT GCT GCA TTC TGC TTG TTT TTC TTC CTC GAG CGT       864
Met Arg Phe Pro Pro Ala Ala Phe Cys Leu Phe Phe Phe Leu Glu Arg
                275                 280                 285

TAC GGC CTG TCT TCG ATG AGG CCG TTC CCA AAT CCC GGC ACA GTC GAC       912
Tyr Gly Leu Ser Ser Met Arg Pro Phe Pro Asn Pro Gly Thr Val Asp
            290                 295                 300

ACT TAC TTG GTC TAC CAA GGC GTC CAA TAC ATG TGG AAA GCC GGG CAG       960
```

-continued

```
                    Thr Tyr Leu Val Tyr Gln Gly Val Gln Tyr Met Trp Lys Ala Gly Gln
                        305                 310                 315

CTG CCA CCG AAG CTG TTC CAT CGC GTT TAC AAC GGT TGG CGT GCG TTC                  1008
Leu Pro Pro Lys Leu Phe His Arg Val Tyr Asn Gly Trp Arg Ala Phe
320                 325                 330                 335

TTG AAG GAC GGT TTC TAT GAG CGA GAT ATT GTG TTG GCT TCG CCT GTC                  1056
Leu Lys Asp Gly Phe Tyr Glu Arg Asp Ile Val Leu Ala Ser Pro Val
                340                 345                 350

GCT ATT ACT CAG GCC TTG AAA TCA GGA GAC ATT AGG TGG GCT CAT GAC                  1104
Ala Ile Thr Gln Ala Leu Lys Ser Gly Asp Ile Arg Trp Ala His Asp
            355                 360                 365

TCC TGG CAA ATT TGG CTG AAC CGT TTC GGG AGG GAG TCC TTC TCT TCA                  1152
Ser Trp Gln Ile Trp Leu Asn Arg Phe Gly Arg Glu Ser Phe Ser Ser
        370                 375                 380

GGG ATA GAG AGG ATC TTT CTG GGC ACA CAT CCT CCT GGT GGT GAA ACA                  1200
Gly Ile Glu Arg Ile Phe Leu Gly Thr His Pro Pro Gly Gly Glu Thr
385                 390                 395

TGG AGT TTT CCT CAT GAT TGG GAC CTA TTC AAG CTA ATG GGA ATA GGA                  1248
Trp Ser Phe Pro His Asp Trp Asp Leu Phe Lys Leu Met Gly Ile Gly
400                 405                 410                 415

TCT GGC GGG TTT GGT CCA GTT TTT GAA AGC GGG TTT ATT GAG ATC CTC                  1296
Ser Gly Gly Phe Gly Pro Val Phe Glu Ser Gly Phe Ile Glu Ile Leu
                420                 425                 430

CGC TTG GTC ATC AAC GGA TAT GAA GAA AAT CAG CGG ATG TGC CCT GAA                  1344
Arg Leu Val Ile Asn Gly Tyr Glu Glu Asn Gln Arg Met Cys Pro Glu
            435                 440                 445

GGA ATC TCA GAA CTT CCA CGT CGG ATC GCA TCT GAA GTG GTT AAC GGT                  1392
Gly Ile Ser Glu Leu Pro Arg Arg Ile Ala Ser Glu Val Val Asn Gly
        450                 455                 460

GTG TCT GTG AGC CAG CGC ATA TGC CAT GTT CAA GTC AGG GCG ATT CAG                  1440
Val Ser Val Ser Gln Arg Ile Cys His Val Gln Val Arg Ala Ile Gln
465                 470                 475

AAG GAA AAG ACA AAA ATA AAG ATA AGG CTT AAG AGC GGG ATA TCT GAA                  1488
Lys Glu Lys Thr Lys Ile Lys Ile Arg Leu Lys Ser Gly Ile Ser Glu
480                 485                 490                 495

CTT TAT GAT AAG GTG GTG GTC ACA TCT GGA CTC GCA AAT ATC CAA CTC                  1536
Leu Tyr Asp Lys Val Val Val Thr Ser Gly Leu Ala Asn Ile Gln Leu
                500                 505                 510

AGG CAT TGC CTG ACA TGC GAT ACC AAT ATT TTT CAG GCA CCA GTG AAC                  1584
Arg His Cys Leu Thr Cys Asp Thr Asn Ile Phe Gln Ala Pro Val Asn
            515                 520                 525

CAA GCG GTT GAT AAC AGC CAT ATG ACA GGA TCG TCA AAA CTC TTC CTG                  1632
Gln Ala Val Asp Asn Ser His Met Thr Gly Ser Ser Lys Leu Phe Leu
        530                 535                 540

ATG ACT GAA CGA AAA TTC TGG TTA GAC CAT ATC CTC CCG TCT TGT GTC                  1680
Met Thr Glu Arg Lys Phe Trp Leu Asp His Ile Leu Pro Ser Cys Val
545                 550                 555

CTC ATG GAC GGG ATC GCA AAA GCA GTG TAT TGC CTG GAC TAT GAG CCG                  1728
Leu Met Asp Gly Ile Ala Lys Ala Val Tyr Cys Leu Asp Tyr Glu Pro
560                 565                 570                 575

CAG GAT CCG AAT GGT AAA GGT CTA GTG CTC ATC AGT TAT ACA TGG GAG                  1776
Gln Asp Pro Asn Gly Lys Gly Leu Val Leu Ile Ser Tyr Thr Trp Glu
                580                 585                 590

GAC GAC TCC CAC AAG CTG TTG GCG GTC CCC GAC AAA AAA GAG CGA TTA                  1824
Asp Asp Ser His Lys Leu Leu Ala Val Pro Asp Lys Lys Glu Arg Leu
            595                 600                 605

TGT CTG CTG CGG GAC GCA ATT TCG AGA TCT TTC CCG GCG TTT GCC CAG                  1872
Cys Leu Leu Arg Asp Ala Ile Ser Arg Ser Phe Pro Ala Phe Ala Gln
        610                 615                 620
```

```
CAC CTA TTT CCT GCC TGC GCT GAT TAC GAC CAA AAT GTT ATT CAA CAT         1920
His Leu Phe Pro Ala Cys Ala Asp Tyr Asp Gln Asn Val Ile Gln His
    625                 630                 635

GAT TGG CTT ACA GAC GAG AAT GCC GGG GGA GCT TTC AAA CTC AAC CGG         1968
Asp Trp Leu Thr Asp Glu Asn Ala Gly Gly Ala Phe Lys Leu Asn Arg
640                 645                 650                 655

CGT GGT GAG GAT TTT TAT TCT GAA GAA CTT TTC TTT CAA GCA CTG GAC         2016
Arg Gly Glu Asp Phe Tyr Ser Glu Glu Leu Phe Phe Gln Ala Leu Asp
                660                 665                 670

ACG GCT AAT GAT ACC GGA GTT TAC TTG GCG GGT TGC AGT TGT TCC TTC         2064
Thr Ala Asn Asp Thr Gly Val Tyr Leu Ala Gly Cys Ser Cys Ser Phe
            675                 680                 685

ACA GGT GGA TGG GTG GAG GGT GCT ATT CAG ACC GCG TGT AAC GCC GTC         2112
Thr Gly Gly Trp Val Glu Gly Ala Ile Gln Thr Ala Cys Asn Ala Val
        690                 695                 700

TGT GCA ATT ATC CAC AAT TGT GGA GGC ATT TTG GCA AAG GGC AAT CCT         2160
Cys Ala Ile Ile His Asn Cys Gly Gly Ile Leu Ala Lys Gly Asn Pro
    705                 710                 715

CTC GAA CAC TCT TGG AAG AGA TAT AAC TAC CGC ACT AGA AAT TAG             2205
Leu Glu His Ser Trp Lys Arg Tyr Asn Tyr Arg Thr Arg Asn *
720                 725                 730

GAGCTC                                                                  2211
```

(2) INFORMATION FOR SEQ ID NO:3:

(i) SEQUENCE CHARACTERISTICS:
        (A) LENGTH: 733 amino acids
        (B) TYPE: amino acid
        (D) TOPOLOGY: linear (ii) MOLECULE TYPE: protein (xi) SEQUENCE DESCRIPTION: SEQ ID NO:3:

```
Met Val Asp Lys Ala Asp Glu Leu Asp Arg Arg Val Ser Asp Ala Phe
1               5                   10                  15

Leu Glu Arg Glu Ala Ser Arg Gly Arg Arg Ile Thr Gln Ile Ser Thr
                20                  25                  30

Glu Cys Ser Ala Gly Leu Ala Cys Lys Arg Leu Ala Asp Gly Arg Phe
            35                  40                  45

Pro Glu Ile Ser Ala Gly Lys Val Ala Val Leu Ser Ala Tyr Ile
        50                  55                  60

Tyr Ile Gly Lys Glu Ile Leu Gly Arg Ile Leu Glu Ser Lys Pro Trp
65                  70                  75                  80

Ala Arg Ala Thr Val Ser Gly Leu Val Ala Ile Asp Leu Ala Pro Phe
                85                  90                  95

Cys Met Asp Phe Ser Glu Ala Gln Leu Ile Gln Ala Leu Phe Leu Leu
                100                 105                 110

Ser Gly Lys Arg Cys Ala Pro Ile Asp Leu Ser His Phe Val Ala Ile
            115                 120                 125

Ser Ile Ser Lys Thr Ala Gly Phe Arg Thr Leu Pro Met Pro Leu Tyr
        130                 135                 140

Glu Asn Gly Thr Met Lys Cys Val Thr Gly Phe Thr Ile Thr Leu Glu
145                 150                 155                 160

Gly Ala Val Pro Phe Asp Met Val Ala Tyr Gly Arg Asn Leu Met Leu
                165                 170                 175

Lys Gly Ser Ala Gly Ser Phe Pro Thr Ile Asp Leu Leu Tyr Asp Tyr
            180                 185                 190

Arg Pro Phe Phe Asp Gln Cys Ser Asp Ser Gly Arg Ile Gly Phe Phe
```

-continued

```
            195                 200                     205
Pro Glu Asp Val Pro Lys Pro Lys Val Ala Val Ile Gly Ala Gly Ile
    210                 215                 220

Ser Gly Leu Val Val Ala Asn Glu Leu Leu His Ala Gly Val Asp Asp
225                 230                 235                 240

Val Thr Ile Tyr Glu Ala Ser Asp Arg Val Gly Gly Lys Leu Trp Ser
                245                 250                 255

His Ala Phe Arg Asp Ala Pro Ser Val Val Ala Glu Met Gly Ala Met
                260                 265                 270

Arg Phe Pro Pro Ala Ala Phe Cys Leu Phe Phe Leu Glu Arg Tyr
                275                 280                 285

Gly Leu Ser Ser Met Arg Pro Phe Pro Asn Pro Gly Thr Val Asp Thr
    290                 295                 300

Tyr Leu Val Tyr Gln Gly Val Gln Tyr Met Trp Lys Ala Gly Gln Leu
305                 310                 315                 320

Pro Pro Lys Leu Phe His Arg Val Tyr Asn Gly Trp Arg Ala Phe Leu
                325                 330                 335

Lys Asp Gly Phe Tyr Glu Arg Asp Ile Val Leu Ala Ser Pro Val Ala
                340                 345                 350

Ile Thr Gln Ala Leu Lys Ser Gly Asp Ile Arg Trp Ala His Asp Ser
                355                 360                 365

Trp Gln Ile Trp Leu Asn Arg Phe Gly Arg Glu Ser Phe Ser Ser Gly
    370                 375                 380

Ile Glu Arg Ile Phe Leu Gly Thr His Pro Pro Gly Gly Glu Thr Trp
385                 390                 395                 400

Ser Phe Pro His Asp Trp Asp Leu Phe Lys Leu Met Gly Ile Gly Ser
                405                 410                 415

Gly Gly Phe Gly Pro Val Phe Glu Ser Gly Phe Ile Glu Ile Leu Arg
                420                 425                 430

Leu Val Ile Asn Gly Tyr Glu Glu Asn Gln Arg Met Cys Pro Glu Gly
                435                 440                 445

Ile Ser Glu Leu Pro Arg Arg Ile Ala Ser Glu Val Val Asn Gly Val
    450                 455                 460

Ser Val Ser Gln Arg Ile Cys His Val Gln Val Arg Ala Ile Gln Lys
465                 470                 475                 480

Glu Lys Thr Lys Ile Lys Ile Arg Leu Lys Ser Gly Ile Ser Glu Leu
                485                 490                 495

Tyr Asp Lys Val Val Thr Ser Gly Leu Ala Asn Ile Gln Leu Arg
                500                 505                 510

His Cys Leu Thr Cys Asp Thr Asn Ile Phe Gln Ala Pro Val Asn Gln
                515                 520                 525

Ala Val Asp Asn Ser His Met Thr Gly Ser Ser Lys Leu Phe Leu Met
                530                 535                 540

Thr Glu Arg Lys Phe Trp Leu Asp His Ile Leu Pro Ser Cys Val Leu
545                 550                 555                 560

Met Asp Gly Ile Ala Lys Ala Val Tyr Cys Leu Asp Tyr Glu Pro Gln
                565                 570                 575

Asp Pro Asn Gly Lys Gly Leu Val Leu Ile Ser Tyr Thr Trp Glu Asp
                580                 585                 590

Asp Ser His Lys Leu Leu Ala Val Pro Asp Lys Lys Glu Arg Leu Cys
                595                 600                 605

Leu Leu Arg Asp Ala Ile Ser Arg Ser Phe Pro Ala Phe Ala Gln His
    610                 615                 620
```

-continued

```
Leu Phe Pro Ala Cys Ala Asp Tyr Asp Gln Asn Val Ile Gln His Asp
625                 630                 635                 640

Trp Leu Thr Asp Glu Asn Ala Gly Gly Ala Phe Lys Leu Asn Arg Arg
                645                 650                 655

Gly Glu Asp Phe Tyr Ser Glu Glu Leu Phe Phe Gln Ala Leu Asp Thr
            660                 665                 670

Ala Asn Asp Thr Gly Val Tyr Leu Ala Gly Cys Ser Cys Ser Phe Thr
        675                 680                 685

Gly Gly Trp Val Glu Gly Ala Ile Gln Thr Ala Cys Asn Ala Val Cys
    690                 695                 700

Ala Ile Ile His Asn Cys Gly Gly Ile Leu Ala Lys Gly Asn Pro Leu
705                 710                 715                 720

Glu His Ser Trp Lys Arg Tyr Asn Tyr Arg Thr Arg Asn
                725                 730
```

(2) INFORMATION FOR SEQ ID NO:4:

(i) SEQUENCE CHARACTERISTICS:
        (A) LENGTH: 745 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 3..725

(xi) SEQUENCE DESCRIPTION: SEQ ID NO:4:

```
CC ATG GAC CTG CAT CTA ATT TTC GGT CCA ACT TGC ACA GGA AAG ACG        47
   Met Asp Leu His Leu Ile Phe Gly Pro Thr Cys Thr Gly Lys Thr
   1               5                   10                  15

ACG ACC GCG ATA GCT CTT GCC CAG CAG ACA GGG CTT CCA GTC CTT TCG        95
Thr Thr Ala Ile Ala Leu Ala Gln Gln Thr Gly Leu Pro Val Leu Ser
                20                  25                  30

CTT GAT CGG GTC CAA TGC TGT CCT CAA CTA TCA ACC GGA AGC GGA CGA       143
Leu Asp Arg Val Gln Cys Cys Pro Gln Leu Ser Thr Gly Ser Gly Arg
            35                  40                  45

CCA ACA GTG GAA GAA CTG AAA GGA ACG ACG CGT CTC TAC CTT GAT GAT       191
Pro Thr Val Glu Glu Leu Lys Gly Thr Thr Arg Leu Tyr Leu Asp Asp
        50                  55                  60

CGG CCT CTG GTG GAG GGT ATC ATC GCA GCC AAG CAA GCT CAT CAT AGG       239
Arg Pro Leu Val Glu Gly Ile Ile Ala Ala Lys Gln Ala His His Arg
65                  70                  75

CTG ATC GAG GAG GTG TAT AAT CAT GAG GCC AAC GGC GGG CTT ATT CTT       287
Leu Ile Glu Glu Val Tyr Asn His Glu Ala Asn Gly Gly Leu Ile Leu
    80                  85                  90                  95

GAG GGA GGA TCC ACC TCG TTG CTC AAC TGC ATG GCG CGA AAC AGC TAT       335
Glu Gly Gly Ser Thr Ser Leu Leu Asn Cys Met Ala Arg Asn Ser Tyr
                100                 105                 110

TGG AGT GCA GAT TTT CGT TGG CAT ATT ATT CGC CAC AAG TTA CCC GAC       383
Trp Ser Ala Asp Phe Arg Trp His Ile Ile Arg His Lys Leu Pro Asp
            115                 120                 125

CAA GAG ACC TTC ATG AAA GCG GCC AAG GCC AGA GTT AAG CAG ATG TTG       431
Gln Glu Thr Phe Met Lys Ala Ala Lys Ala Arg Val Lys Gln Met Leu
        130                 135                 140
```

```
CAC CCC GCT GCA GGC CAT TCT ATT ATT CAA GAG TTG GTT TAT CTT TGG      479
His Pro Ala Ala Gly His Ser Ile Ile Gln Glu Leu Val Tyr Leu Trp
    145                 150                 155

AAT GAA CCT CGG CTG AGG CCC ATT CTG AAA GAG ATC GAT GGA TAT CGA      527
Asn Glu Pro Arg Leu Arg Pro Ile Leu Lys Glu Ile Asp Gly Tyr Arg
160                 165                 170                 175

TAT GCC ATG TTG TTT GCT AGC CAG AAC CAG ATC ACG GCA GAT ATG CTA      575
Tyr Ala Met Leu Phe Ala Ser Gln Asn Gln Ile Thr Ala Asp Met Leu
                180                 185                 190

TTG CAG CTT GAC GCA AAT ATG GAA GGT AAG TTG ATT AAT GGG ATC GCT      623
Leu Gln Leu Asp Ala Asn Met Glu Gly Lys Leu Ile Asn Gly Ile Ala
            195                 200                 205

CAG GAG TAT TTC ATC CAT GCG CGC CAA CAG GAA CAG AAA TTC CCC CAA      671
Gln Glu Tyr Phe Ile His Ala Arg Gln Gln Glu Gln Lys Phe Pro Gln
        210                 215                 220

GTT AAC GCA GCC GCT TTC GAC GGA TTC GAA GGT CAT CCG TTC GGA ATG      719
Val Asn Ala Ala Ala Phe Asp Gly Phe Glu Gly His Pro Phe Gly Met
    225                 230                 235

TAT TAG GTTACGCCAG CCCTGAGCTC                                         745
Tyr *
240
```

(2) INFORMATION FOR SEQ ID NO:5:

(i) SEQUENCE CHARACTERISTICS:
        (A) LENGTH: 240 amino acids
        (B) TYPE: amino acid
        (D) TOPOLOGY: linear (ii) MOLECULE TYPE: protein (xi) SEQUENCE DESCRIPTION: SEQ ID NO:5:

```
Met Asp Leu His Leu Ile Phe Gly Pro Thr Cys Thr Gly Lys Thr Thr
1               5                   10                  15

Thr Ala Ile Ala Leu Ala Gln Gln Thr Gly Leu Pro Val Leu Ser Leu
            20                  25                  30

Asp Arg Val Gln Cys Cys Pro Gln Leu Ser Thr Gly Ser Gly Arg Pro
        35                  40                  45

Thr Val Glu Glu Leu Lys Gly Thr Thr Arg Leu Tyr Leu Asp Asp Arg
    50                  55                  60

Pro Leu Val Glu Gly Ile Ile Ala Ala Lys Gln Ala His His Arg Leu
65                  70                  75                  80

Ile Glu Glu Val Tyr Asn His Glu Ala Asn Gly Gly Leu Ile Leu Glu
                85                  90                  95

Gly Gly Ser Thr Ser Leu Leu Asn Cys Met Ala Arg Asn Ser Tyr Trp
            100                 105                 110

Ser Ala Asp Phe Arg Trp His Ile Ile Arg His Lys Leu Pro Asp Gln
        115                 120                 125

Glu Thr Phe Met Lys Ala Ala Lys Ala Arg Val Lys Gln Met Leu His
    130                 135                 140

Pro Ala Ala Gly His Ser Ile Ile Gln Glu Leu Val Tyr Leu Trp Asn
145                 150                 155                 160

Glu Pro Arg Leu Arg Pro Ile Leu Lys Glu Ile Asp Gly Tyr Arg Tyr
                165                 170                 175

Ala Met Leu Phe Ala Ser Gln Asn Gln Ile Thr Ala Asp Met Leu Leu
            180                 185                 190

Gln Leu Asp Ala Asn Met Glu Gly Lys Leu Ile Asn Gly Ile Ala Gln
        195                 200                 205
```

```
Glu Tyr Phe Ile His Ala Arg Gln Gln Glu Gln Lys Phe Pro Gln Val
    210                 215                 220

Asn Ala Ala Ala Phe Asp Gly Phe Glu Gly His Pro Phe Gly Met Tyr
225                 230                 235                 240
```

(2) INFORMATION FOR SEQ ID NO:6:

(i) SEQUENCE CHARACTERISTICS:
        (A) LENGTH: 498 base pairs
        (B) TYPE: nucleic acid
        (C) STRANDEDNESS: double
        (D) TOPOLOGY: Not Relevant (ii) MOLECULE TYPE: cDNA (iii) HYPOTHETICAL: NO (xi) SEQUENCE DESCRIPTION: SEQ ID NO:6:

```
ATTGAGAGGT ACAAGAAGCA CCATGCTGAT TCCACCAGTC AAGGGTCTGT TTCTGAATCT    60

AACACTCAGT ATTACCAGCA AGAAGCAGCC AAACTGCGAC GACAAATACG AGATATACAG   120

ACTTATAACA GGCAAATAGT TGGAGAGGCC CTGAGCAGTT TAAGCCCTAG GGACCTAAAG   180

AATTTGGAAG GAAACTTGA GAAGGCCATT GGTAGAGTCC GTTCCAAAAA GAATGAATTG   240

CTCTTCTCAG AAATTGAGCT CATGCAAAAG AGGGAGATTA ATCTGCAGAA TGCCAACATG   300

TGTCTACGAG CAAAGATAGC GGAGGTAGAG AGAGCACAAC AGCAAATGAA CTTGATGCCA   360

GGAGGATCTG AATACAATCA GCAGCAGCAG CCAATGACTA CTTCTCAGAA TTATAACGAT   420

GCTCGCAACT TCCTGCCTGT AAATCTGCTG GAACCTAATC CCCATTACTC TCGCCACGAC   480

GACCAAACCG CTCTCCAG                                                 498
```

(2) INFORMATION FOR SEQ ID NO:7:

(i) SEQUENCE CHARACTERISTICS:
        (A) LENGTH: 1051 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (xi) SEQUENCE DESCRIPTION: SEQ ID NO:7:

```
GAAAATGATG AGGAATGGGC AAAACACAAA AGAGTTTCCT TTCGTAACTA CAATTAATTA    60

ATGCAAATCT GAGAAAGGGT TCATGGATAA TGACTACACA CATGATTAGT CATTCCCCGT   120

GGGCTCTCTG CTTTCATTTA CTTTATTAGT TTCATCTTCT CTAATTATAT TGTCGCATAT   180

GATGCAGTTC TTTTGTCTAA ATTACGTAAT ATGATGTAAT TAATTATCAA AATAATATTA   240

ACGACATGCA ATGTATATAG GAGTAGGGCA ATAAAAAGAA AAGGAGAATA AAAAGGGATT   300

ACCAAAAAAG GAAAGTTTCC AAAAGGTGAT TCTGATGAGA AACAGAGCCC ATACCTCTCT   360

TTTTTCCTCT AAACATGAAA GAAAAATTGG ATGGTCCTCC TTCAATGCTC TCTCCCCACC   420

CAATCCAAAC CCAACTGTCT TCTTTCTTTC TTTTTTCTTC TTTCTATTTG ATATTTTCTA   480

CCACTTAATT CCAATCAATT TCAAATTTCA ATCTAAATGT ATGCATATAG GAATTTAATT   540

AAAAGAATTA GGTGTGTGAT ATTTGAGAAA ATGTTAGAAG TAATGGTCCA TGTTCTTTCT   600

TTCTTTTTCC TTCTATAACA CTTCAGTTTG AAAAAAAACT ACCAAACCTT CTGTTTTCTG   660

CAAATGGGTT TTTAAATACT TCCAAAGAAA TATTCCTCTA AAAGAAATTA TAAACCAAAA   720

CAGAAACCAA AACAAAAAA TAAAGTTGAA GCAGCAGTTA AGTGGTACTG AGATAATAAG   780
```

-continued

```
AATAGTATCT TTAGGCCAAT GAACAAATTA ACTCTCTCAT AATTCATCTT CCCATCCTCA      840

CTTCTCTTTC TTTCTGATAT AATTAATCTT GCTAAGCCAG GTATGGTTAT TGATGATTTA      900

CACTTTTTTT TAAAAGTTTC TTCCTTTTCT CCAATCAAAT TCTTCAGTTA ATCCTTATAA      960

ACCATTTCTT TAATCCAAGG TGTTTGAGTG CAAAAGGATT TGATCTATTT CTCTTGTGTT     1020

TATACTTCAG CTAGGGCTTA TATAGAAAAT G                                    1051
```